United States Patent [19]
Turner, Jr. et al.

[11] 4,302,355
[45] Nov. 24, 1981

[54] PLATELET REFERENCE CONTROL

[75] Inventors: James E. Turner, Jr., Morristown; Michael B. Kenoff, Hackettstown, both of N.J.

[73] Assignee: Warner-Lambert Company, Morris Plains, N.J.

[21] Appl. No.: 130,781

[22] Filed: Mar. 4, 1980

Related U.S. Application Data

[63] Continuation of Ser. No. 23,130, Mar. 23, 1979, abandoned, which is a continuation-in-part of Ser. No. 821,063, Aug. 1, 1977, abandoned.

[51] Int. Cl.$^3$ .................... C09K 3/00; G01N 33/16
[52] U.S. Cl. .................... 252/408; 23/230 B; 424/3; 424/8; 424/12; 424/101
[58] Field of Search .................... 252/408; 23/230 B; 424/3, 8, 12, 101

[56] References Cited

U.S. PATENT DOCUMENTS

| | | | |
|---|---|---|---|
| 3,632,735 | 1/1972 | Kita | 424/3 |
| 3,634,581 | 1/1972 | Thomas | 252/408 |
| 3,640,896 | 2/1972 | De Casperis | 252/408 |
| 3,714,345 | 1/1973 | Hirata | 252/408 |
| 3,873,467 | 3/1975 | Hunt | 252/408 |
| 3,884,579 | 5/1975 | Mauthner | 252/408 |
| 3,973,913 | 8/1976 | Louderback et al. | 252/408 |
| 3,977,995 | 8/1976 | Louderback et al. | 252/408 |
| 4,145,185 | 3/1979 | Brinkhous et al. | 252/408 |
| 4,157,383 | 6/1979 | Sedlacek et al. | 252/408 |
| 4,160,644 | 7/1979 | Ryan | 252/408 |

FOREIGN PATENT DOCUMENTS 2551208  5/1977  Fed. Rep. of Germany ...... 252/408

*Primary Examiner*—Teddy S. Gron
*Attorney, Agent, or Firm*—Stephen I. Miller

[57] ABSTRACT

This invention describes a novel method for preparing a stable suspension of individual blood platelets for use as a control in both manual and automatic platelet counting procedures.

8 Claims, No Drawings

PLATELET REFERENCE CONTROL

This is a continuation of application Ser. No. 023,130, filed Mar. 23, 1979, now abandoned, which is a continuation-in-part of U.S. Ser. No. 821,063, filed Aug. 1, 1977, now abandoned.

Hematology laboratories require platelet reference standards and controls to maintain quality control of their platelet counting instrumentation and techniques which under present methods for counting involve both manual procedures, such as phase contrast microscopy, and automated techniques using electronic particle counters. Both the manual procedure and the automatic technique require enumeration of single platelets.

Presently, a few laboratories are using platelet rich plasma suspensions which are freshly prepared for control purposes.

Blood platelets, however, are difficult to count under phase contrast microscopy because of their small size (about 2–4 microns), furthermore, platelets have a strong tendency to clump together and form aggregates. When platelets come in contact with a wettable surface, such as glass or plastic, they lose their oval or rounded shape; numerous pseudopods appear from the cell membrane surface and within a short time the platelets coalesce into numerous amorphic aggregates. As a result, this makes it difficult, if not impossible, for a clinical hematology laboratory to maintain an accurate and reproducible platelet reference suspension.

A desired platelet reference control should, obviously, consist of a suspension of individual unaggregated platelets. In order to obtain such a stable suspension of individual platelets, it is necessary to completely inhibit platelet aggregation.

We have demonstrated that a successful approach to inhibit platelet aggregation is to utilize compounds that will fix and stabilize the platelet membrane by forming cross-links between protein functional groups. A family of compounds which will accomplish this type of fixation are the aldehydes, such as glutaraldehyde, which readily reacts with amino, imino, guanidyl, hydroxyl, carboxyl, and SH groups of the protein molecule. Another family of compounds which we have discovered are capable of forming cross-links with proteins on the platelet surface are chromium salts, such as potassium, sodium, lithium, ammonium, calcium, and barium dichromate. In the presence of water, chromium salts form complexes of the type —Cr—O—Cr— which will combine with reactive groups on adjacent protein chains to bring about a cross-link affect similar to that of aldehydes.

The object of our invention is to use mixtures of aldehydes and chromium salts to prepare a stable suspension of individual blood platelets.

We have found that optimal conditions for fixing platelets are obtained when aldehyde is added to undiluted platelet rich plasma at a concentration between 0.05 to 0.15% (w/v). Furthermore, we have found that the presence of dichromate at concentrations between 0.20 to 0.30% (w/v) improves the stability of the platelet suspension. Superior suspensions of fixed platelets are obtained when platelets are fixed with both compounds simultaneously.

Optimal conditions for fixed platelets are obtained when glutaraldehyde is added to undiluted platelet rich plasma at a concentration of 0.05 to 0.15% (w/v), preferably 0.1 (w/v), and potassium dichromate at a concentration of 0.22% (w/v).

The method for preparing a platelet reference control according to our invention is given in the following examples: Temperatures referred to are in degrees centigrade.

EXAMPLE 1

Preparation of Platelet Rich Plasma

Fresh whole blood was drawn through siliconized needles into plastic syringes and immediately tranferred to a polypropylene tube containing one-sixth volume of ACD solution (2.5 g. sodium citrate, 1.3 g. citric acid, 2.0 g. dextrose, g.s. to 100 ml. with water). The tube was capped, inverted and centrifuged at 66×g for 25 minutes. The platelet rich plasma was then removed from the other blood cells by aspiration and transferred to a clean polypropylene tube.

EXAMPLE 2

Fixation of Platelets

To each 0.5 ml. aliquot of platelet rich plasma prepared in accordance with Example 1 was added in succession and with gentle swirling 50μl of 2.5% (w/v) potassium dichromate solution and 10μl of glutaraldehyde solution prepared by diluting a 25% (w/v) glutaraldehyde stock solution with physiological saline to a concentration of 5.0% (w/v). The resulting solution containing glutaraldehyde at a final concentration of 0.1% (w/v) and potassium dichromate at a final concentration of 0.22% (w/v) was incubated for 1 hour at 37° C.

EXAMPLE 3

Resuspension of Platelets

Method A

Platelets fixed according to Example 2 were removed from suspension by centrifugation. Platelets were immediately resuspended in 0.5 ml. of a physiological saline solution containing Human Serum Albumin at a concentration of 2.5% (w/v).

Method B

Platelets fixed according to Example 2 were removed from suspension by centrifugation. Platelets were immediately resuspended in 0.5 ml. of a physiological saline solution containing Dimethyl Sulfoxide at a concentration of 20% (v/v).

Method C

Platelets fixed according to Example 2 were removed from suspension by centrifugation. Platelets were immediately resuspended in 0.5 ml. of physiological saline.

When the glutaraldehyde concentration was varied in the absence of potassium dichromate (Example 2, omitting the dichromate solution), optimal fixing conditions were achieved only when the glutaraldehyde concentration was 0.1% (w/v). Concentrations of glutaraldehyde above or below 0.1% (w/v) without dichromate significantly increased platelet aggregation as determined with a light microscope. Concentrations greater than 0.15% (w/v) glutaraldehyde resulted in gel formation in the platelet rich plasma.

When varying quantities of glutaraldehyde were added to platelet rich plasma containing 0.22% (w/v) potassium dichromate, the suspensions containing 0.05% (w/v) to 0.15% (w/v) glutaraldehyde showed no aggregation. Glutaraldehyde concentrations of more than 0.15% (w/v) or less than 0.05% (w/v), however, resulted in significant platelet aggregation and concentrations greater than 0.2% (w/v) gelled the platelet rich plasma.

In order to determine the effect of varying the temperature and time of fixation, platelet rich plasma suspensions were fixed as in Example 2 for thirty minutes to three hours at four different temperatures ranging from 20° C. to 56° C. The fixed platelets were resuspended in a 7.5% (w/v) human serum albuminsaline solution and monitored microscopically for the degree of aggregation which occurred during three month storage at room temperature.

Human serum albumin-suspended platelets prepared by fixing at temperatures between 30° C. and 40° C. exhibited no aggregation. Suspensions of platelets fixed at either 20° C., 45° C. or 56° C. exhibited a marked reduction in the number of unaggregated platelets. Varying the time of fixation between 1 and 3 hours had no significant effect.

In order to determine whether stable suspensions of fixed platelets could also be prepared in other protein solutions, the fixed platelets were resuspended, as in Example 3A, in normal human serum and saline solutions containing different concentrations (1.25 to 7.5% w/v) of human serum albumin. Following two-week storage at room temperature, only the human serum albumin-suspended fixed platelets were stable.

In order to determine if stable suspensions of fixed platelets also could be prepared in non-protein solutions, fixed platelets were resuspended in physiological saline (Example 3C) and in saline solutions containing different dimethyl sulfoxide (DMSO) concentrations ranging from 2.5 to 20% (v/v) (Example 3B).

Fixed platelets suspended in physiological saline or 2.5% to 20% (v/v) DMSO were stable for at least seven weeks.

We claim:

1. A method of preparing a stable suspension of unaggregated blood platelets which comprises adding dichromate salt to an amount of platelet rich plasma and adding glutaraldehyde to the dichromatic-platelet rich plasma mixture to a final concentration of between 0.2-0.3% (w/v) of dichromate salt and between 0.05-0.15% (w/v) glutaraldehyde and incubating the resultant suspension at a temperature of 30°-40° C. for an effective period of time.

2. The method according to claim 1 wherein the aldehyde is at a concentration of 0.1% (w/v) and the dichromate is at a concentration of 0.22% (w/v).

3. A suspension of blood platelets made in accordance with claim 1.

4. A method of preparing a stable suspension of unaggregated blood platelets which comprises:
  i. Adding a dichromate salt to a platelet rich plasma and adding glutaraldehyde to the dichromate-platelet rich plasma to a final concentration of between 0.2-0.3% (w/v) of dichromate salt and between 0.05-0.15% (w/v) glutaraldehyde;
  ii. Allowing the suspension so prepared to react for 30 to 180 minutes at a temperature of 30° C. to 40° C.;
  iii. Removing the fixed platelets; and
  iv. Resuspending the platelets in a solution selected from the following group consisting of:
    (a) physiological saline containing serum albumin at a concentration of 1.25% to 7.5% (w/v); (b) dimethylsulfoxide diluted with physiological saline to a concentration of 2.5% to 20% (v/v); and (c) physiological saline.

5. The method of claim 4 wherein the dichromate is potassium dichromate.

6. The method of claim 5 wherein the resuspending solution is 20% (v/v) dimethyl sulfoxide.

7. The method of claim 5 wherein the suspension is allowed to react for about 60 minutes.

8. A suspension of blood platelets made in accordance with the method of claim 5.

* * * * *